US012109326B2

(12) United States Patent
Carter et al.

(10) Patent No.: US 12,109,326 B2
(45) Date of Patent: Oct. 8, 2024

(54) DEMINERALIZED BONE FIBER COMPOSITION FOR AUGMENTATION OF FIXATION

(71) Applicant: Theracell, LLC, Hopkinton, MA (US)

(72) Inventors: Andrew J. Carter, Stow, MA (US); Bradley E. Patt, Sherman Oaks, CA (US); Gunnar Andersson, Sherman Oaks, CA (US); Ian McRury, Sherman Oaks, CA (US)

(73) Assignee: Theracell, LLC, Hopkinton, MA (US)

( * ) Notice: Subject to any disclaimer, the term of this patent is extended or adjusted under 35 U.S.C. 154(b) by 616 days.

(21) Appl. No.: 16/638,113

(22) PCT Filed: Aug. 10, 2018

(86) PCT No.: PCT/US2018/046382

§ 371 (c)(1),
(2) Date: Feb. 10, 2020

(87) PCT Pub. No.: WO2019/033082

PCT Pub. Date: Feb. 14, 2019

(65) Prior Publication Data

US 2020/0237960 A1 Jul. 30, 2020

Related U.S. Application Data

(60) Provisional application No. 62/659,086, filed on Apr. 17, 2018, provisional application No. 62/544,582, filed on Aug. 11, 2017.

(51) Int. Cl.
*A61B 17/68* (2006.01)
*A61F 2/08* (2006.01)
(Continued)

(52) U.S. Cl.
CPC ........ *A61L 27/3608* (2013.01); *A61B 17/686* (2013.01); *A61F 2/0811* (2013.01);
(Continued)

(58) Field of Classification Search
CPC .......................... A61L 27/3608; A61B 17/686
See application file for complete search history.

(56) References Cited

U.S. PATENT DOCUMENTS 4,877,864 A 10/1989 Wang et al.
5,013,649 A 5/1991 Wang et al.
(Continued)

FOREIGN PATENT DOCUMENTS

WO 9300432 A1 1/1993
WO 9426892 A1 11/1994
(Continued)

OTHER PUBLICATIONS

International Search Report and Written Opinion for International Application No. PCT/US18/46382 dated Nov. 2, 2018; 6 pgs.
(Continued)

*Primary Examiner* — Brian A Dukert
(74) *Attorney, Agent, or Firm* — Squire Patton Boggs (US) LLP

(57) ABSTRACT

Compositions and methods thereof include bone fibers made from cortical bone in which a plurality of bone fibers are made into shapes that are used to augment fixation of orthopedic implants and screws. Sheets of bone fibers may be used as an interface between bone and tissue, tendons, and/or ligaments. Cylindrical shaped implants that may be placed in drilled holes in bone prior to screw placement to enhance fixation of the screw. The physical presence of the fibers provides initial fixation, while the use of an osteoinductive material provides long term enhancement of bone formation around the screw and hence fixation. The bone
(Continued)

fiber compositions may be in the form of a cylinder or a tube. A delivery system and methods of use are also provided.

9 Claims, 14 Drawing Sheets

(51) Int. Cl.
*A61L 27/36* (2006.01)
*A61B 17/70* (2006.01)

(52) U.S. Cl.
CPC ....... *A61B 17/7001* (2013.01); *A61L 2430/02* (2013.01); *A61L 2430/10* (2013.01)

(56) References Cited

U.S. PATENT DOCUMENTS

| | | | |
|---|---|---|---|
| 5,106,748 | A | 4/1992 | Wozney et al. |
| 5,108,922 | A | 4/1992 | Wang et al. |
| 5,116,738 | A | 5/1992 | Wang et al. |
| 5,366,875 | A | 11/1994 | Wozney et al. |
| 5,439,684 | A | 8/1995 | Prewett et al. |
| 5,716,359 | A * | 2/1998 | Ojima .................. A61L 31/026 606/76 |
| 9,486,557 | B2 | 11/2016 | Carter et al. |
| 9,572,912 | B2 | 2/2017 | Scarborough et al. |
| 9,913,676 | B2 * | 3/2018 | Schlachter .............. A61L 27/54 |
| 2002/0120346 | A1 | 8/2002 | Boyer et al. |
| 2003/0009235 | A1 | 1/2003 | Manrique et al. |
| 2003/0236573 | A1 | 12/2003 | Evans et al. |
| 2008/0027470 | A1 | 1/2008 | Hart et al. |
| 2014/0314822 | A1 * | 10/2014 | Carter ................ A61L 27/3847 264/28 |
| 2016/0367728 | A1 | 12/2016 | Reves et al. |

FOREIGN PATENT DOCUMENTS

| | | | |
|---|---|---|---|
| WO | 9426893 | A1 | 11/1994 |
| WO | 2010016942 | A1 | 2/2010 |
| WO | 2016123583 | A1 | 8/2016 |

OTHER PUBLICATIONS

Examination Report for Australian Patent Application No. 2018313306 dated Aug. 9, 2023, 4 pages.

Smith et al., "Rotator cuff healing using demineralized cancellous bone matrix sponge interposition compared to standard repair in a preclinical canine model", J Orthop Res., 2017, pp. 906-912, 7 pages.

Lovric et al., "Effects of demineralized bone matrix on tendon-bone healing in an intra-articular rodent model", Am J Sports Med., 2012, 40(10), pp. 2365-2374, 10 pages.

Lovric et al., "Demineralized bone matrix augmented tendon-bone healing in transosseous-equivalent sheep rotator cuff model", J. Sci. Med. Sport, 2013, S138. 2 pages.

* cited by examiner

DEMINERALIZED BONE FIBER COMPOSITION FOR AUGMENTATION OF FIXATION

CROSS-REFERENCE TO RELATED APPLICATIONS

The present application claims priority to and the benefit of U.S. Provisional Application Ser. No. 62/544,582 filed on Aug. 11, 2017, entitled "Demineralized Bone Fiber Composition For Augmentation Of Fixation,", and U.S. Provisional Application Ser. No. 62/659,086 filed on Apr. 17, 2018, entitled "Demineralized Bone Fiber Composition For Augmentation Of Fixation," the entire contents of both of which are incorporated herein by reference.

BACKGROUND

Worldwide, osteoporosis causes more than 8.9 million fractures annually, resulting in an osteoporotic fracture every 3 seconds. Osteoporosis is estimated to affect 200 million women worldwide—approximately one-tenth of women aged 60, one-fifth of women aged 70, two-fifths of women aged 80, and two-thirds of women aged 90. Osteoporosis affects an estimated 75 million people in Europe, USA and Japan. For the year 2000, there were an estimated 9 million new osteoporotic fractures, of which 1.6 million were at the hip, 1.7 million were at the forearm and 1.4 million were clinical vertebral fractures. Europe and the Americas accounted for 51% of all these fractures, while most of the remainder occurred in the Western Pacific region and Southeast Asia. Worldwide, 1 in 3 women over age 50 will experience osteoporotic fractures, as will 1 in 5 men over age 50.

Modern spine surgical techniques encounter difficulty in achieving and maintaining fixation in osteoporotic vertebrae in the case of fracture and/or deformity. The bone-screw interface is typically the region most susceptible to loosening and failure. Many physical factors may affect the final fixation strength of pedicle screws such as screw pitch and diameter, yet host factors have at least as much effect. Pedicle screws have been shown to loosen in patients with compromised bone strength arising from renal osteodystrophy and osteoporosis. A significant portion of these cases will sustain catastrophic failure after attempted surgical fixation. As a result, some spine surgeons may refuse to perform stabilization surgery on osteoporotic patients with fractures and/or severe deformities. There have been many attempts to improve the holding capacity of pedicle screw constructs in osteoporotic bone including the addition of various cements for augmentation and the use of novel screw designs such as expandable screws. Use of polymethylmethacrylate (PMMA) cement has been shown to increase pull-out strength up to 150%. Use of cement to augment traditional pedicle screw fixation generally yields increased resistance to pullout and/or toggle failure in the cephalad-caudad direction as reported in numerous studies, but there are associated potential morbidities such as spinal canal extrusion or vascular flow obstruction.

Similar problems of initial fixation strength and subsequent loosening and failure exist with the use of screws in orthopedic procedures such as hip fractures that often occur in patients with osteoporotic or otherwise compromised bone.

Similarly there is a desire for implants to bond effectively and rapidly to surrounding bone, particularly when that bone is compromised. Various strategies are employed to facilitate this including the use of porous ingrowth surfaces. Implant loosening however remains a problem and concern to orthopedists.

When tendon or ligament tissues or grafts are placed either in apposition to bone, as in the case of rotator cuff repair or in bone tunnels as in anterior cruciate ligament repair, the creation or recreation of the tendon-bone enthesis is a problem and concern to orthopedists.

SUMMARY OF INVENTION

Aspects of embodiments of the present invention are directed to a means of improving the fixation of implants and tissue to bone through the use of an implant, which may, for example, be composed of fibers of demineralized bone and formed into an appropriate shape. The implant according to some embodiments of the present invention may be placed at the interface between the tissue and bone or may be placed in a hole of a bone prior to insertion of a screw.

In some embodiments of the present invention, a means of improving the fixation of screws in bone through the use of an implant is disclosed and is, for example, composed of fibers of demineralized bone that are formed into an appropriate shape. Using the implant, kits, and/or methods as disclosed herein, the implant is placed in the hole in the bone to be repaired. More specifically, the implant is placed in the hole of the bone in which a bone screw it to be placed. By placing the implant in the hole of the bone prior to the insertion of the screw, the implant contacts the implant and provides a more dense substance into which the screw may be secured, thereby increasing the insertion torque and the force required to pull the screw back out of the hole. As such, the implant provided in the hole of a bone prior to insertion of a bone screw decreases the chances of the screw being able to dislodge from the hole and allows for a more secure and effective bone repair. demineralized bone fibers (DBF) are both osteoinductive and osteoconductive, there is an additional benefit of the DBF implant providing an increase in the local bone growth around the implant and further increasing the likelihood of a long term and possibly permanent bone repair. The benefits of this DBF implant are of particular relevance when the screw is being implanted into osteoporotic bone or into an existing screw hole, as in the case of revision surgery.

According to some embodiments of the present invention, methods of water-assisted molding of DBF allow for more facile fabrication of implants for use in augmentation of screw fixation In some embodiments of the present invention, the implant is placed at the interface between a tissue implant such as an autologous or allogeneic tissue graft used for ligament reconstruction and the bone tunnel into which the graft is intended to integrate. The implant according to some embodiments of the present invention serves to improve the integration in these graft repairs.

In some embodiments of the present invention, the implant is placed at the interface between a torn rotator cuff tissue and the bone. The implant according to some embodiments of the present invention serves to improve the integration between the tendon and bone and facilitate recreation of the enthesis.

FIG. **15*a* shows a variant of the implant for augmentation of screw fixation (31**) wherein the implant is in the form of a rectangular prism, according to some embodiments of the present invention.

FIG. **15*b* shows a variant of the implant of the present disclosure, where a central portion (32**) is densified to provide it with increased strength, according to some embodiments of the present invention.

FIG. **15*c* shows a variant of the implant of the present disclosure where the cross-section (33**) is semi-circular, according to some embodiments of the present invention.

FIG. **15*d* shows a variant of the implant of the present disclosure where the rectangular prism is narrower at the center (34**), according to some embodiments of the present invention.

FIG. **15*e* shows a variant of the implant of the present disclosure where; the rectangular prism is both narrower at the center (34) and possesses a semi-circular cross-section (33**), according to some embodiments of the present invention.

FIG. **15*f* shows a variant of the implant of the present disclosure where a side view cross-section of a drill hole (35) with an implant (31) inserted, the insertion being effected by use of a pusher (36**), where the implant is longer than is required to fit the hole, according to some embodiments of the present invention.

FIG. **15*g* shows a side view cross-section of a drill hole (35) with an implant (31) of the present disclosure inserted, the insertion being effected by use of a pusher (36**), Where the implant is the exact length that is required to fit the hole, according to some embodiments of the present invention.

Figure 15A:
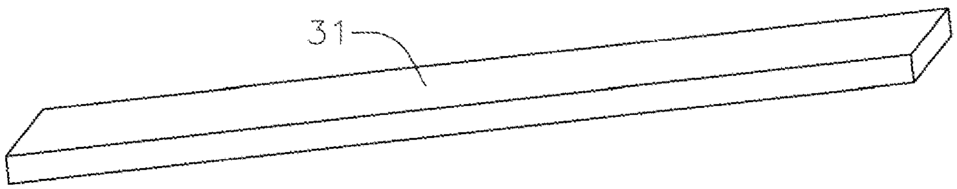
Figure 15B:
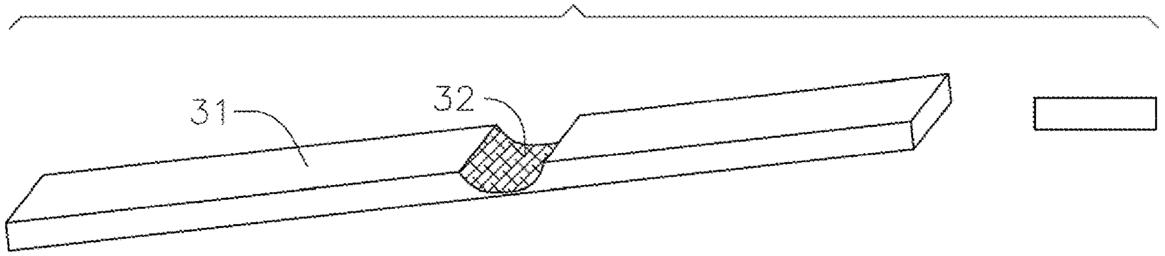
Figure 15C:
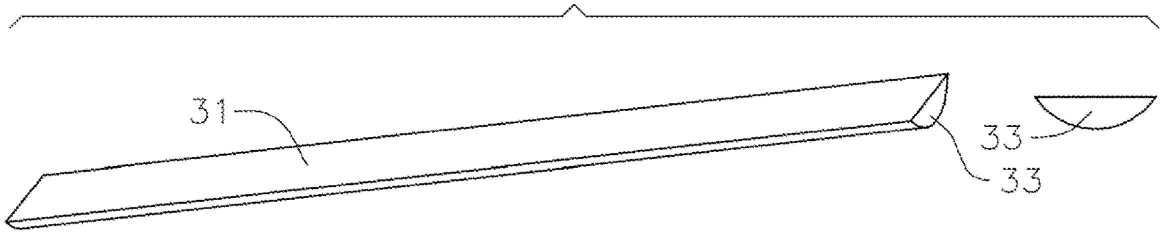

FIG. **15*h* is an end view of the implant of FIG. 15*c*** looking down the hole to show the implant forms a space-filling implant when inserted, according to some embodiments of the present invention.

Figure 15D:
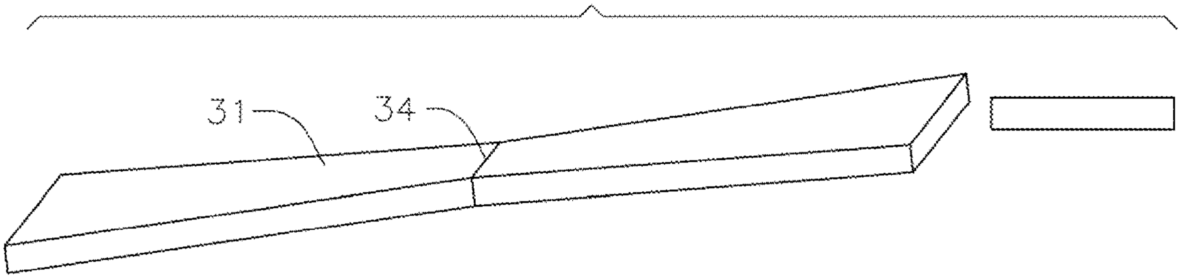
Figure 15E:
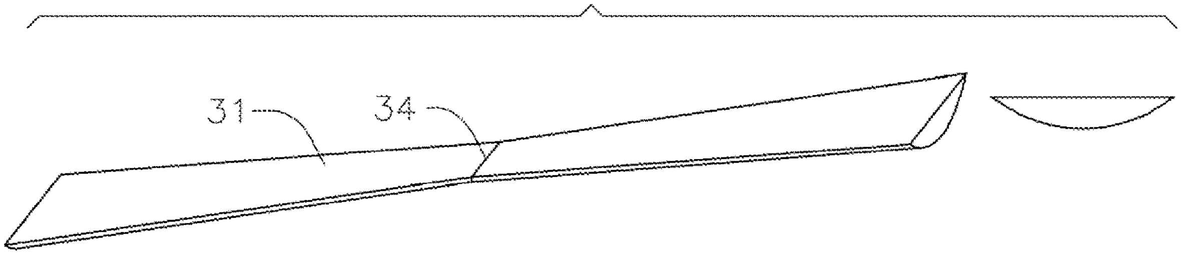

FIG. **15*i* is a cross-sectional view of the implant of FIG. 15*e*** in a tapered hole where the shape of the implant forms a space-filling implant in the tapered hole, according to embodiments of the present invention.

Figure 16:
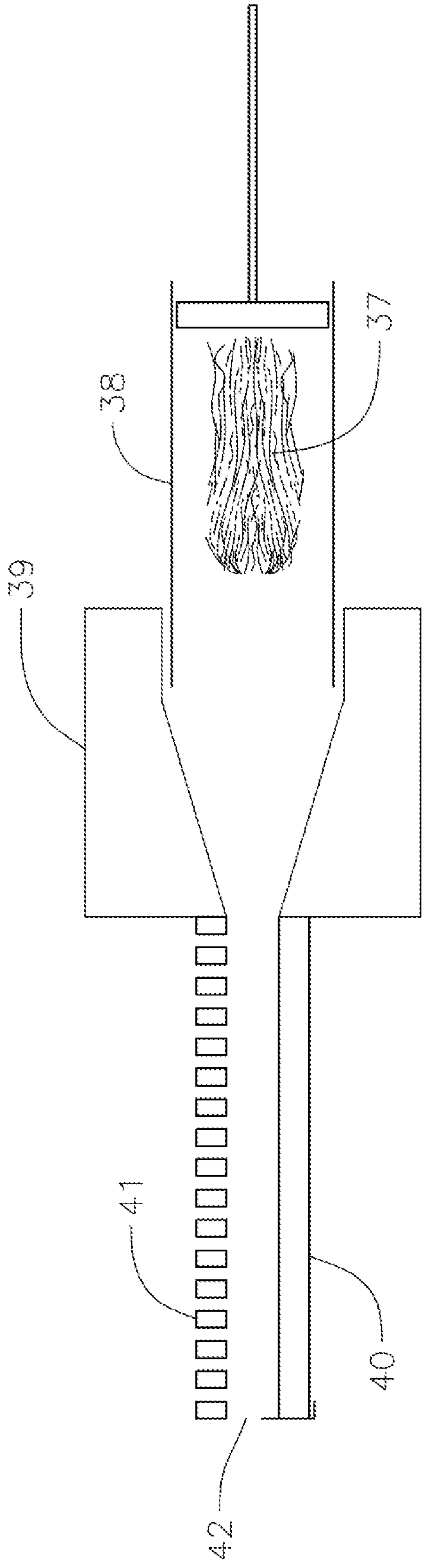

FIG. 16 shows a cross-section view of an apparatus for water assisted injection molding of DBF fibers, where the DBF fibers (37) are loaded into a syringe (38), the distal end of the syringe is fitted into an adapter (39), attached to which is a detachable mold (40), where the mold is tapered towards its distal end and has vents (41) along its length, and a removable vented end cap (42), and the detachable mold is removed after DBF injection and placed into an oven or lyophilizer for drying, according to some embodiments of the present invention.

Figure 17:
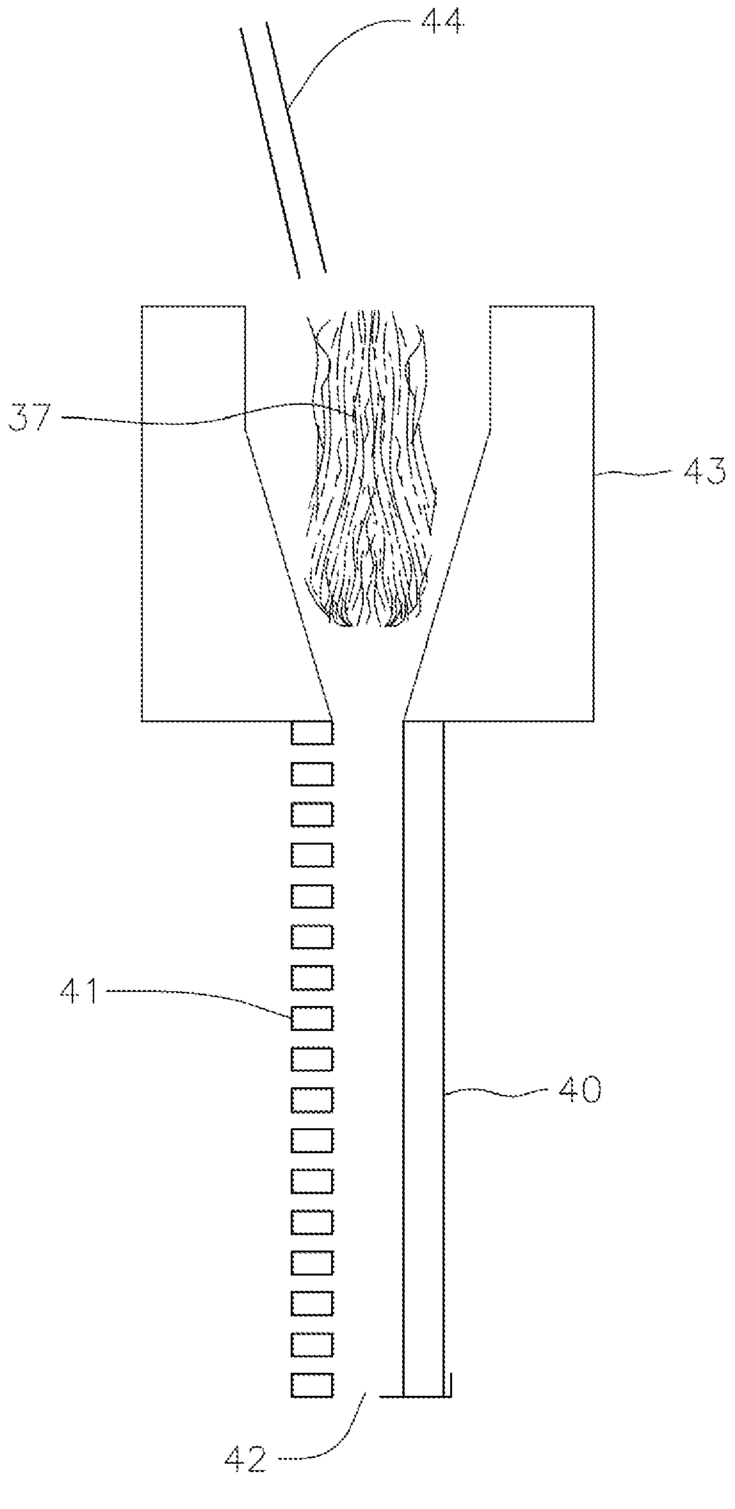

FIG. 17 shows a cross-section view of an apparatus for water jet assisted injection molding of DBF fibers, where the DBF fibers (37) are loaded into a hopper (43), the hopper being attached to a detachable mold (40), the mold tapered toward its distal end having vents (41) along its length, and a removable vented end cap (41), where the water jet (44) is activated to force the DBF from the hopper and into the mold, and the detachable mold is removed after DBF injection and placed into an oven or lyophilizer for drying, according to some embodiments of the present invention.

DETAILED DESCRIPTION

Aspects of the embodiments of the present invention are directed to an approach for augmenting bone repair and healing using demineralized bone fiber (DBF) implants.

In some aspects, embodiments of the present invention include DBF implants, methods of forming DBF implants, and kits including suitably shaped and sized cylindrical DBF implants for augmenting the fixation of screws in osteoporotic or otherwise compromised bone. This approach includes a cylinder of demineralized bone fibers (DBF™) that may be inserted into a hole in a bone in need of repair for the implant to be placed together with and prior to the placement of a bone screw. The cylinder is sized to be the same diameter as the screw hole. At the time of surgery the presence of the device increases the torque required to insert the screw and increases the pull out force that would be required to displace the screw. The additional benefit of using the DBF material is that it is osteoinductive and will cause an increase in local bone formation around the screw providing long term enhancement of fixation. The DBF implant is placed into the hole of the bone prior to insertion of the screw.

In other aspects, embodiments of the present invention include DBF implants, methods forming DBF implants, and kits including suitably formed DBF implants for use as an interface between the bone and the ligament or tendon to be repaired. For example, a sheet of DBF may be used in the bone tunnels of a soft tissue ligament replacement such as an acl (anterior cruciate ligament) surgery where a hamstring or tendon autograft is fixed into a bone tunnel. Additionally, a sheet of DBF may also be used in a rotator cuff repair in which the DBF sheet is placed onto the bone bed between the bone and the tendon to be reattached.

As used herein "implant," "DBF implant," "implant of the present disclosure," and like terms are used interchangeably to refer to a suitably shaped demineralized bone fiber implant made using demineralized bone fibers (DBF) as disclosed herein and disclosed in U.S. Pat. Nos. 9,486,557 and 9,572,912, and WO 2016/123583, the entire contents of all of which are incorporated herein by reference. For example, as shown throughout the present disclosure, suitably shaped DBF implant includes a sheet of DBF or a cylinder-shaped form of DBF.

The popularity of demineralized bone matrix (DBM)-based products is based on the ability to induce bone formation through expression of inherent non-collagenous proteins that stimulate some cell types present at the graft site to differentiate into bone forming cells. This induction of bone formation process is referred to as "osteoinduction" and is due to the natural presence of bone morphogenic proteins (BMPs). DBM also provides a scaffold for these cells to populate and spread throughout in a process known as "osteoconduction." Demineralized bone in the form of a fiber, known as Demineralized Bone Fiber (DBF) has a physical form that has been shown to optimize and enhance the osteoconductive performance of DBM. In some embodiments of the present invention, a composition and method of manufacture of DBF fibers is as disclosed in U.S. Pat. Nos. 9,486,557 and 9,572,912, supra. When DBM or DBF is combined with osteogenic cells that are capable of forming bone, the three mechanisms of bone healing (e.g., osteoinduction, osteoconduction, and osteogenesis) are combined.

The DBF implant is dried so that the implant has sufficient rigidity to allow it to be pushed into a pre formed hole. The DBF fibers may be easily formed into any of the required implant shapes using molding or wet laying processes prior to drying. Optionally a heating step may be utilized which has been shown to impart even greater cohesion to formed DBF implants without affecting the implant's osteoinductivity.

Figure 2:
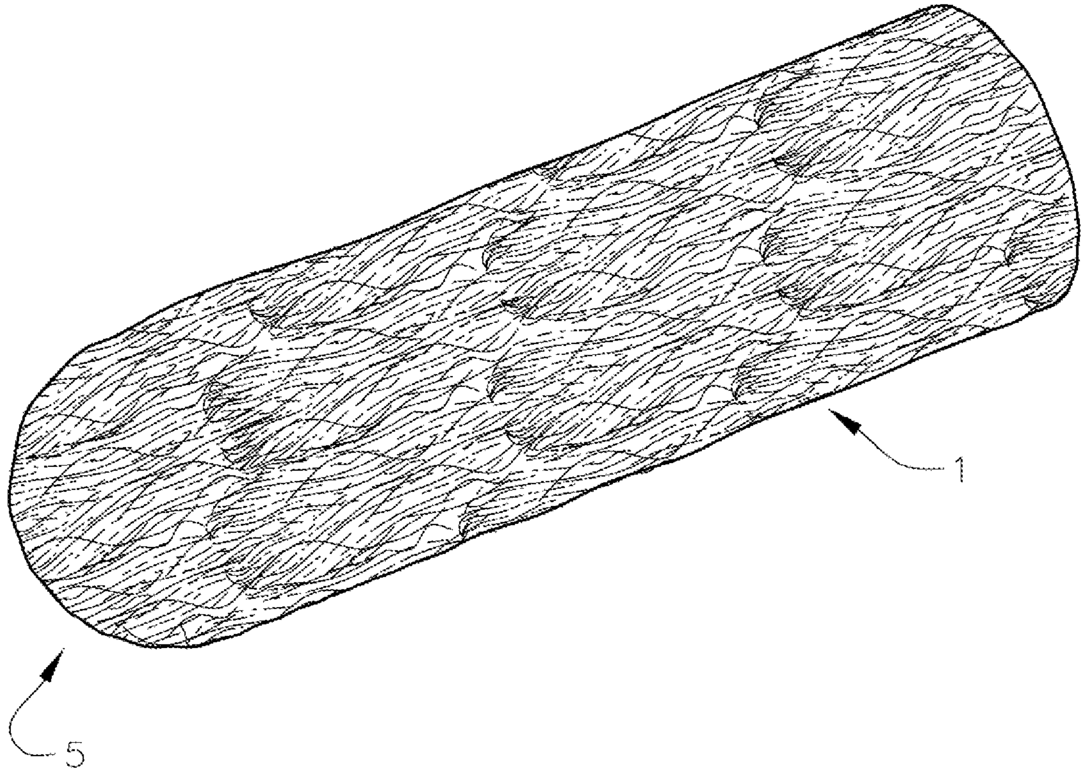
FIG. 2 shows a variant of the implant (1) wherein the front of the cylinder has a domed shape (5) to facilitate insertion, according to some embodiments of the present invention.
Figure 3:
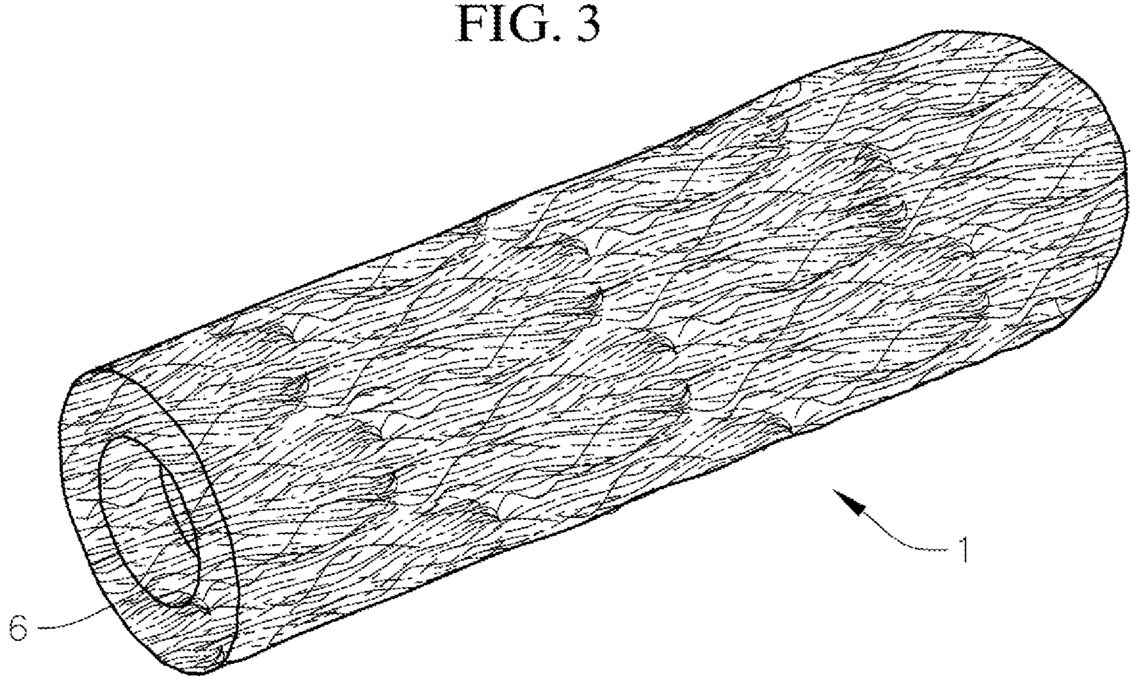
FIG. 3 shows a variant of the implant (1) wherein the rear of the cylinder has a central depression (6) to facilitate insertion of the screw centrally in the implant, according to some embodiments of the present invention.
Figure 13:
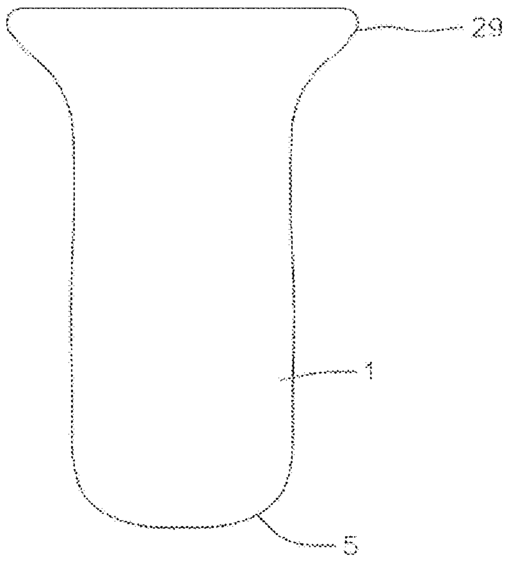
FIG. 13 shows a cross sectional view of a variant of the implant for augmentation of screw fixation (1) wherein in addition to the domed end (5) to aid insertion there is an expanded proximal portion of the implant (29), according to some embodiments of the present invention.

Variations and sophistications to the design include shaping or doming of the distal end of the DBF implant to aid in insertion of the DBF implant into the hole of the bone. An example of such a design is exemplified in DBF implant (5) of FIG. 2. In some embodiments, the proximal end of the DBF implant may also be flared (29) in FIG. 13. This feature may help prevent the implant from being pushed too far into a drilled hole. It will also provide additional DBF fibers at the cortex of the bone and may facilitate healing of that region of the bone.

Figure 14A:
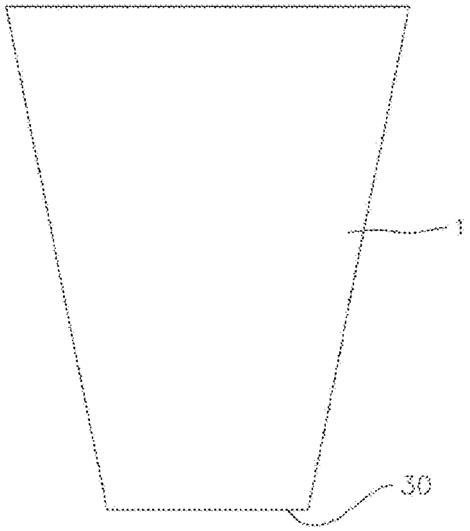
FIG. 14A shows a cross sectional view of a variant of the implant for augmentation of screw fixation (1) wherein the implant is of a narrower diameter at its distal end (30), according to some embodiments of the present invention.
Figure 14B:
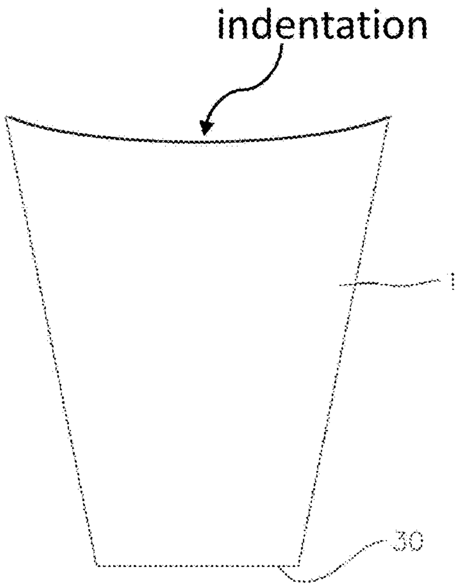
FIGS. 14B and 14C show other embodiments of the present invention.
Figure 14C:
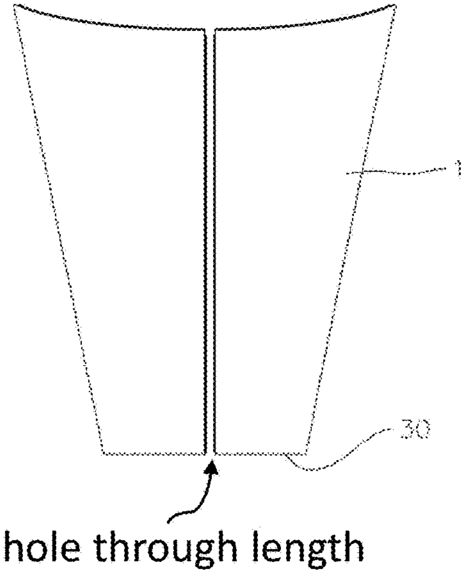

The implant may also be a non-uniform cylinder such that the distal end (30), as shown in the cross-sectional view in FIG. 14 is narrower than the proximal end of the implant. The implant is placed into the hole prior to insertion of the screw.

An implant in the shape of a rectangular prism (31) as shown in FIG. 15*a* may also be used for augmentation of screw fixation. The rectangular prisms may be formed individually or may be cut from a sheet of material (18) that has been formed in a mold. A simple rod (36) may be used to aid insertion of the implant into a drill hole. Densification of an area (32) of the implant may be done to provide a strengthened area to aid insertion. An implant (31) in the shape of a rectangular prism with a semi-circular cross section (33) allows for more effective filling of the hole. This can be seen in FIG. 15*h* which is a top view of an implant (31) with a semi-circular cross section (33) placed in a drill hole (35). The implant is placed into the hole prior to insertion of the screw.

In some instances it will be desired to place an implant in the hole created when a screw is removed from bone, such as in a revision procedure, or in a hole created by an awl. In these cases the distal end of the hole will generally be a smaller diameter than the proximal end. An implant with a shape such as is shown in FIG. 15*d* or 15) is designed to be used in this instance. The implant is placed into the hole prior to insertion of the screw.

Figure 1:
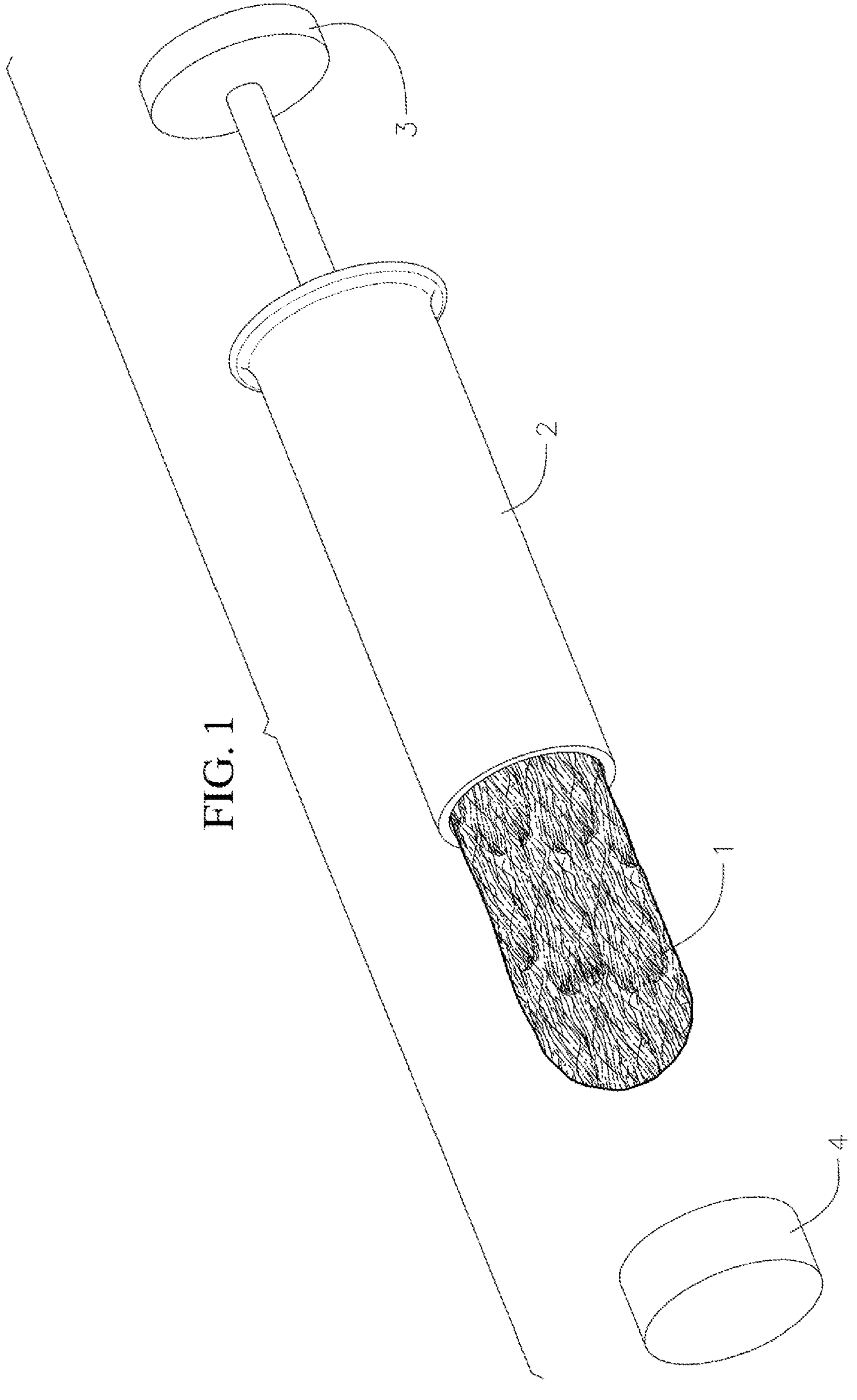
FIG. 1 shows an implant for augmentation of screw fixation and delivery device, according to embodiments of the present invention where the implant (1) is placed in the tubular portion of the delivery instrument (2) and is expelled from the device using the plunger (3) where an optional protective cap (4) may be included and is removed prior to use.

While implants according to embodiments of the present invention may be easily placed into drilled holes by hand, it is envisaged that in some instances it may be desired to have the implant that is provided to the surgeon to be pre-loaded into a syringe like device implant shown in FIG. 1. As is shown in this figure, the implant (1) is held in the body of the syringe (2). In this embodiment, the implant includes a removable cap (4) to maintain the implant in place during storage and transportation, and may optionally have a luer fitting to allow pre hydration of the implant. For implant delivery, the distal end of the syringe is placed over the drill hole and the plunger (3) used to expel the implant. A reusable implant delivery system may also be used.

The hole to receive the implant may be formed by drilling, tapping, or by use of an awl, or may exist through the removal of a screw.

In a variant of an implant according to some embodiments of the present invention, the implant is provided with a hole through its length such that the implant may be delivered over a guide wire.

In other embodiments of the present invention, with reference to FIG. 18, DBF in the form of a thin sheet (18) may also be used to act as an interface between an implant and surrounding bone. The DBF sheet will facilitate conformity of the implant to the surrounding bone and will subsequently, through its osteoinductive nature, stimulate bone formation and integration of the surrounding tissue with the implant.

DBF in the form of a hydrated thin sheet may also be pressed onto the surface of a screw or implant prior to implantation for similar effect.

Figure 10:
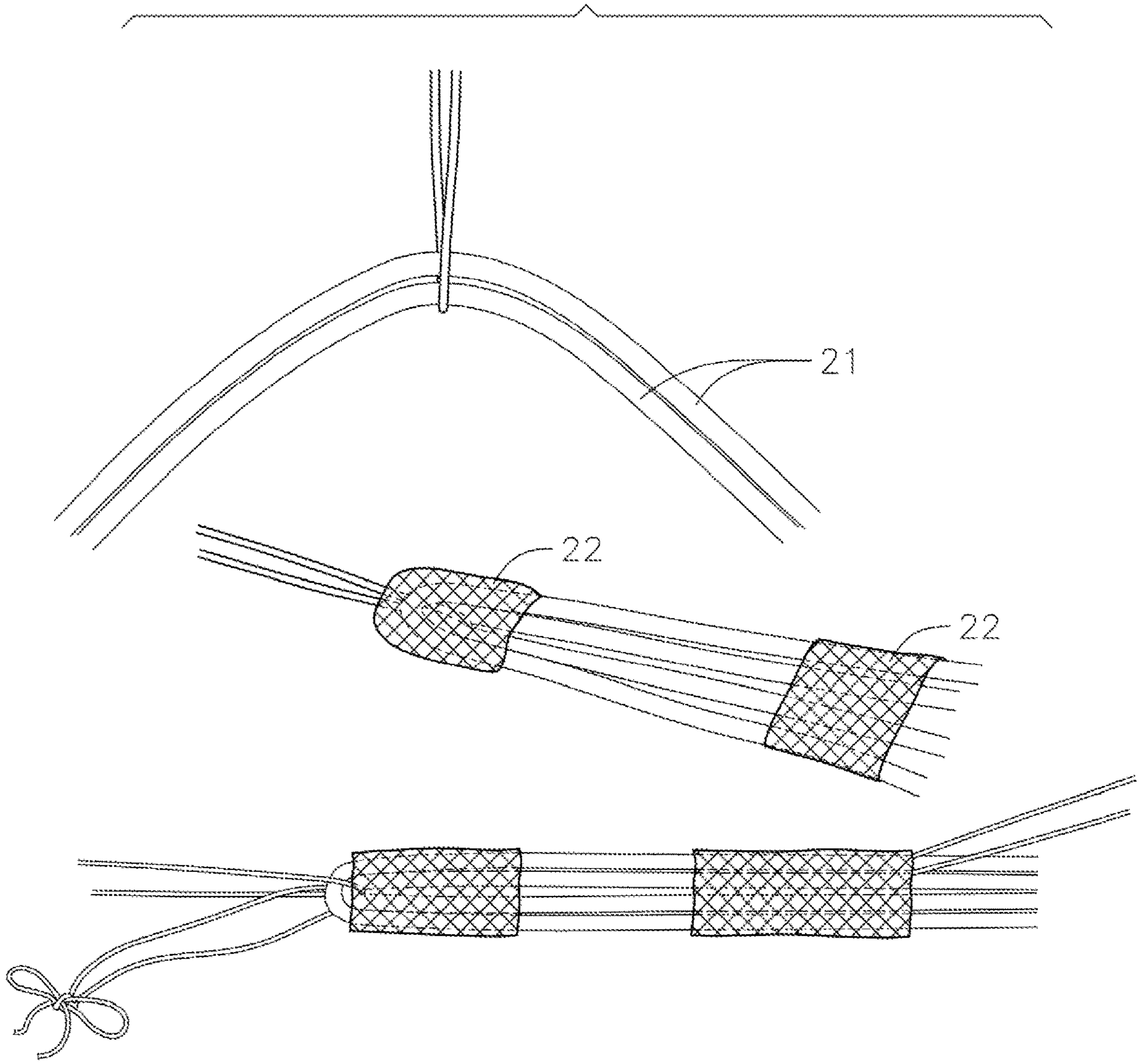
FIG. 10 shows a hamstring graft (21) with a DBF sheet (22) sutured into the regions of the graft destined for the bone tunnels, according to some embodiments of the present invention.

DBF in the form of a thin sheet may also be used to stimulate bone formation in the bone tunnels of a soft tissue ligament replacement such as an acl (anterior cruciate ligament) surgery where a hamstring or tendon autograft is fixed into a bone tunnel. In this usage, as shown in FIG. 10 a sheet of DBF (22) may be sutured onto the hamstring graft (21)

prior to implantation into the patient with the DBF positioned so that it is in tunnel portion of the graft, and may optionally be hydrated to aid its conformity. The osteoinductive nature of the DBF material will stimulate bone to graft healing. The sheet may be simply wrapped around the outside of the hamstring or tendon bundle or may be incorporated in a way that provides DBF between the individual tendons. Suture may be used to hold the DBF sheet in place and may be whipstitched in place during the existing graft preparation step.

Figure 11:
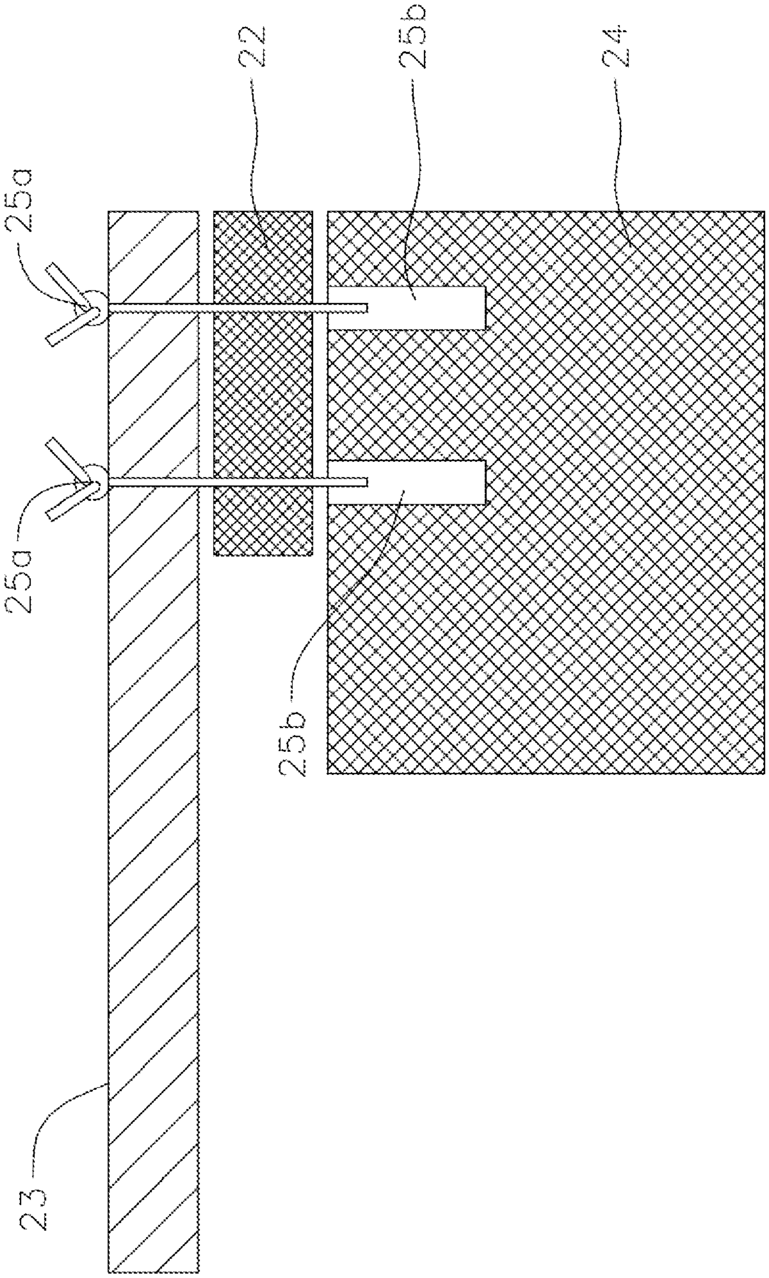
FIG. 11 shows a sheet of DBF (22) placed between the tendon (23) and bone (24). Also shown are sutures (**25*a*) and suture anchors (25*b***) used to reattach the tendon, according to some embodiments of the present invention.
Figure 12:
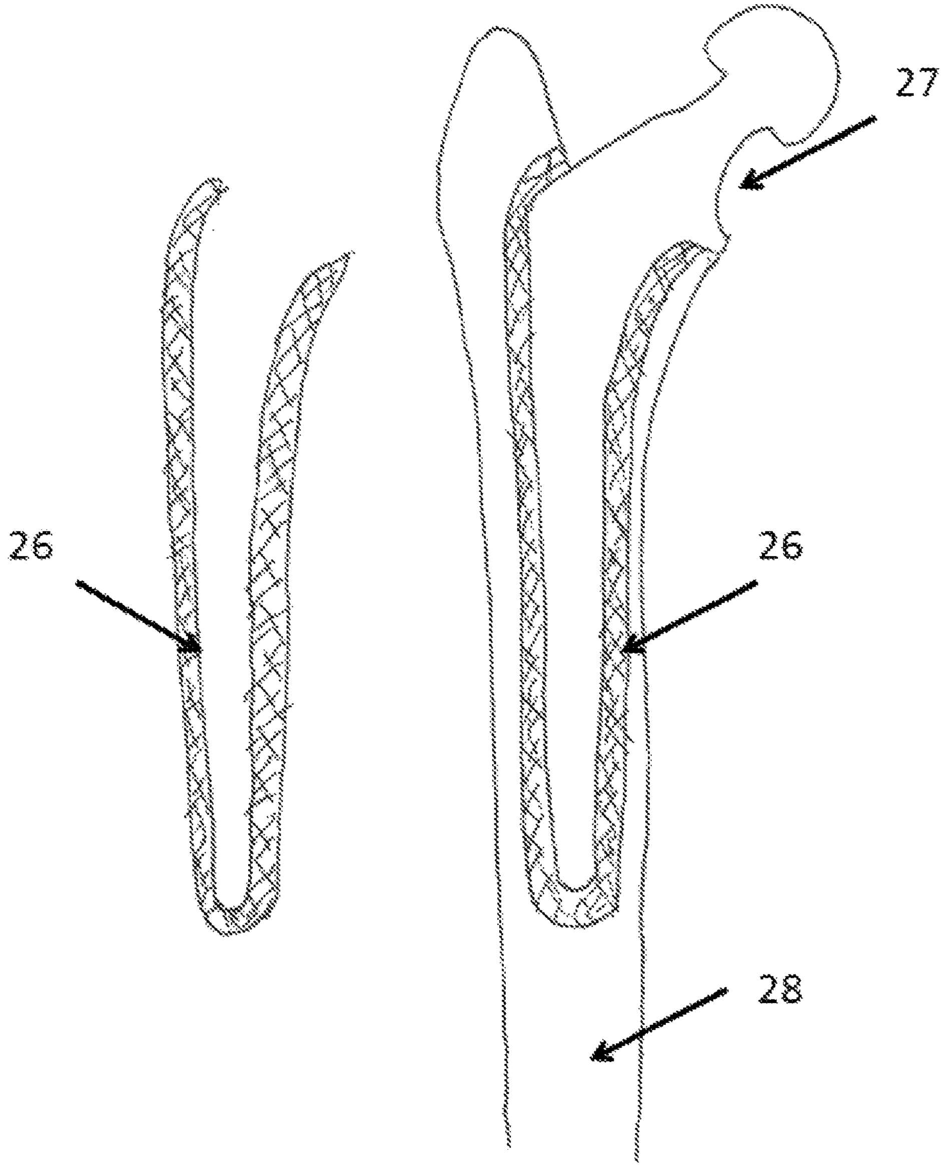
FIG. 12 shows a DBF implant (26) formed in a shape that surrounds the hip stem and forms an interface between the hip stem (27) and surrounding bone (28), according to some embodiments of the present invention.

Augmentation of other tendon and bone interfaces may also be effected by use of sheets of DBF. FIG. 11 is a diagram showing a rotator cuff repair wherein the DBF sheet (22) is placed onto the bone bed between the bone (24) and the tendon to be reattached (23). The nature of the DBF sheet is such that conventional suture anchor fixation techniques do not need to be modified. In FIG. 11 the repair may be seen to be affixed using the sutures (25*a*) together with the suture anchors (25*b*).

In some embodiments of the present invention, a DBF sheet may be used for augmentation of bone-to-bone repair either in a primary fracture repair or in a procedure to remedy a non-union. In these instances, the DBF sheet will form a malleable interface between the two (or more) bone fragments.

A DBF sheet may also be wrapped around the periosteum to hold bone fragments or graft in place in traumatic fractures, and may act as a periosteum substitute. The osteoinductive and osteoconductive nature of the DBF sheet will facilitate healing.

In many joint replacements a stem is placed into a cavity created in the intramedullary canal. It is often desired to enhance the integration of implants such as total hip or shoulder replacements to the surrounding bone. DBF may be formed into a sheath (26) that conforms to the shape of the implant stem (27). The DBF may then provide for augmentation, or stimulation of fixation, of the stem to the surrounding bone.

A further issue that may occur is that, particularly in the case of revision surgery, there is insufficient bone and the surgeon may require the use of bone graft. In these instances the DBF sheath may be provided in a range of thicknesses up to several mm in thickness to provide for use as a bone graft substitute.

In some embodiments of the present invention, the sheet form of DBF may be used to augment the fixation of tibial tray and acetabular cup components of joint replacements. In this latter instance the sheet may be molded into a cup shape.

In some embodiments of the present invention, the DBF used in an implant uses bone that has had the mineral component removed by a demineralization process that renders the graft malleable and not hard. The bone is then further formed into fibers by cutting along the long axis such that the collagen fibers within it are maintained in their natural fibrous form, as disclosed in U.S. Pat. Nos. 9,486,557 and 9,572,912, supra. This material may then be placed into tubes to form the implant device and to facilitate delivery into the screw hole.

A number of methods of forming cylindrical implants from DBF are also disclosed in WO 2016/123583, the entire content of which is herein incorporated by reference.

In some embodiments, the methods for making the bone fibers include demineralizing whole bone and subsequently cutting the demineralized bone in a direction parallel to the orientation of collagen fibers within the demineralized bone to form elongated bone fibers. The bone material of the present invention is derived from human (allograft) or animal (xenograft) cortical bone and is processed in such a manner to provide grafts of high utility based on the controlled geometry of the bone fibers. For veterinary applications bone from the same species. e.g., canine for canine patients (allograft) may be used as well as bone from other species (xenograft). It will be obvious to one skilled in the art that fibers other than demineralized bone fibers may be utilized to make a bone graft of this invention. Such fibers may be made from resorbable polymers or bioactive glasses or mixtures thereof, and may be used in place of or as an additive to the demineralized bone fibers (DBF). The methods of preparation of the graft provide improved efficiency and uniformity with reproducible results and decreased requirements for equipment and resulting costs. The implant device forms according to some embodiments of the present invention do not require the addition of exogenous materials to maintain the form of the graft. These improved characteristics will be apparent to one skilled in the art based upon the present disclosure.

Processing of Fibers.

Processing of the demineralized bone fibers to produce a desired shape or form of the bone fibers may be performed using any suitable method. To make some of these forms, the bone fibers may be collected, ideally in their hydrated state, and compressed using pressure molds, the pressure being sufficient to form the required shape but not so high as to lose the porosity of the fibrous structure. In some embodiments, the bone fibers are formed using a wet lay technique as is well understood by those skilled in the art of nonwoven or paper manufacture. Using a wet lay technique, the cut bone fibers are suspended in an aqueous solution to form a bone fiber slurry. Any suitable biocompatible aqueous solution may be used. Non-limiting examples of biocompatible aqueous solutions include: water, saline, and/or solutions including salts such as phosphate buffered saline (PBS), Ringer's solution, Lactated Ringer's solution, and saline with 5% dextrose. In some embodiments of the present invention, cut fibers are placed into saline to create a slurry of entangled bone fibers. The bone fiber slurry is suspended over a mesh screen (having holes) and the saline is drained resulting in a wet lay process, such that a sheet of demineralized bone fibers is formed on the mesh screen. The screen is contoured to provide a three dimensional shape to the screen such that cylindrical pellets may be directly produced, or is flat so that a sheet is produced. The resulting devices may be then dried using heat and/or vacuum or other means such as lyophilization (freeze-drying). In some embodiments, prior to drying, the sheet is placed in a mold and compressed to a defined thickness and shape, followed by drying. As discussed herein, density, porosity and overall dimensions of the resulting product may be controlled using various molds and techniques.

Figure 4:
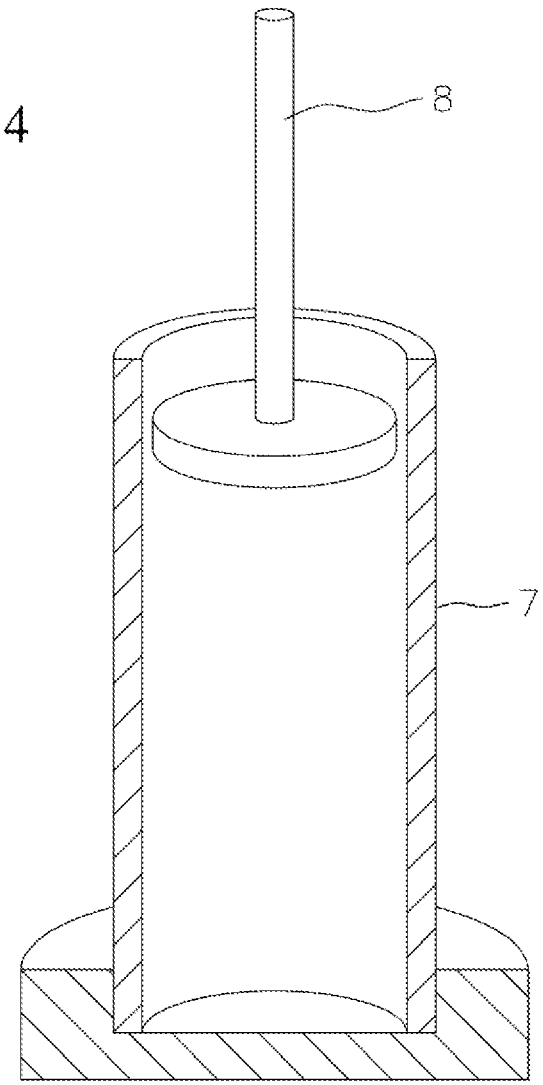
FIG. 4 shows a cylindrical mold (7) and plunger (8) designed to produce cylindrical implants, according to some embodiments of the present invention.
Figure 5:
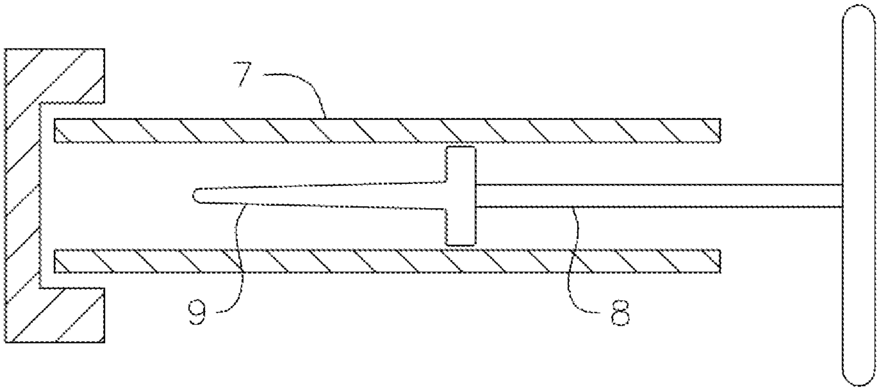
FIG. 5 shows a variant of the mold (7) of FIG. 4 wherein the plunger (8) has a spike (9) that produces a central depression in the implant to facilitate central screw insertion, according to some embodiments of the present invention.
Figure 6:
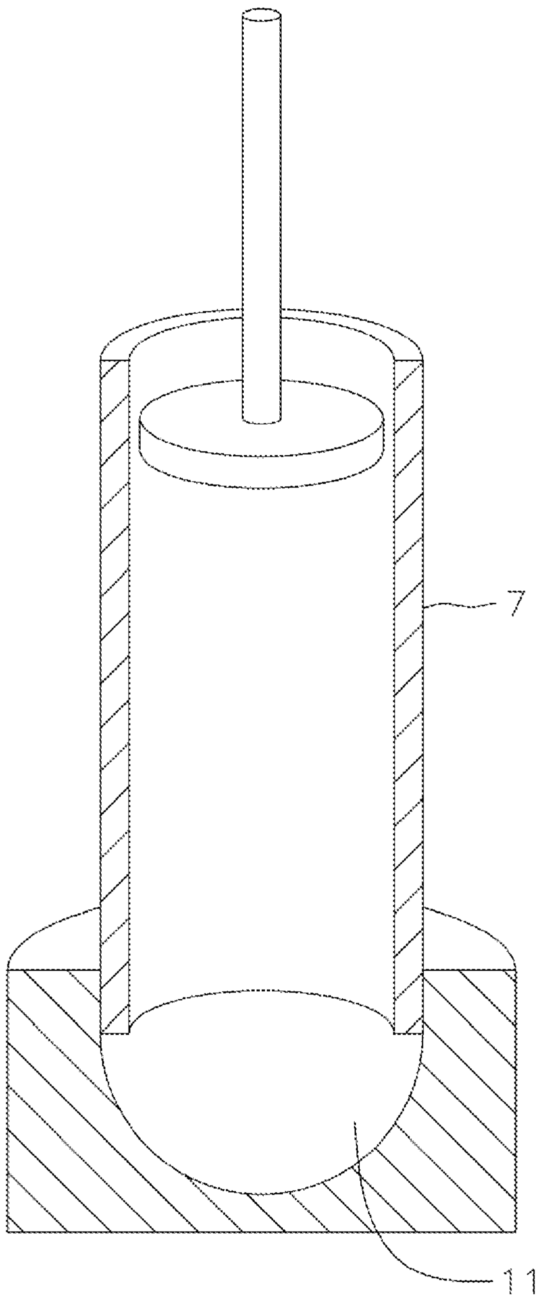
FIG. 6 shows a further variant of the mold (7) of FIG. 4 wherein the distal end of the cylindrical mold (7) has a domed depression (11) to provide a domed implant, according to some embodiments of the present invention.
Figure 9:
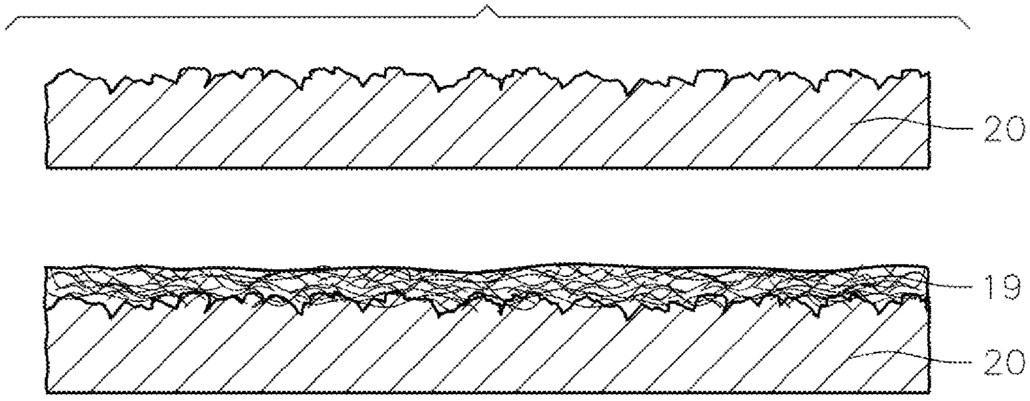
FIG. 9 shows a sheet of DBF (19) formed onto the porous surface of an implant (20), according to some embodiments of the present invention.

Hydrated fibers may also be simply placed into a cylindrical mold cavity and lightly compressed using a plunger or push rod such as is shown in FIGS. 4, 5 and 6. In these variants features are provided to modify the profile of the two ends of the cylindrical mold. A set amount of fiber is introduced into a cylindrical mold and the plunger used to compress the fibers to the required density through control of the depth that the plunger is pushed. Where a plunger has a spike on it, such as is shown in (6) of FIG. 9 the spike may be designed to form a depression, a partial hole, or a hole through the length of the implant. In this latter instance the implant will be in the form of a tube.

In some embodiments a vacuum oven is used, whereby the application of vacuum removes moisture and dries the implant.

In some embodiments the heating step is undertaken by placing the implant in contact with a metal or other high heat-conductivity surface such that the degree of annealing/crosslinking is enhanced at that surface.

In other embodiments, the bone fibers are further processed in a second drying step that may include vacuum drying and/or lyophilization.

In other embodiments the bone fibers may retain some moisture and will be placed in moisture impervious packaging.

In some embodiments the amount of compression, heating, and drying can be tailored to modify the rehydration and re-expansion rates. For example with no heating the rehydration is very fast whereas heating at 45 to 55° C. for approximately one hour causes very slow rehydration and re-expansion. By altering these processes, bone fiber compositions as disclosed herein may retain their manufactured shape during packaging, shipment, unpacking and placement into the graft site, but after placement into the graft site the DBF will begin to absorb moisture rapidly (within 30 seconds or less) and to be completely re-hydrated/re-expanded within approximately 2 minutes, preferably being completely re-hydrated/re-expanded within 30 seconds.

Figure 8:
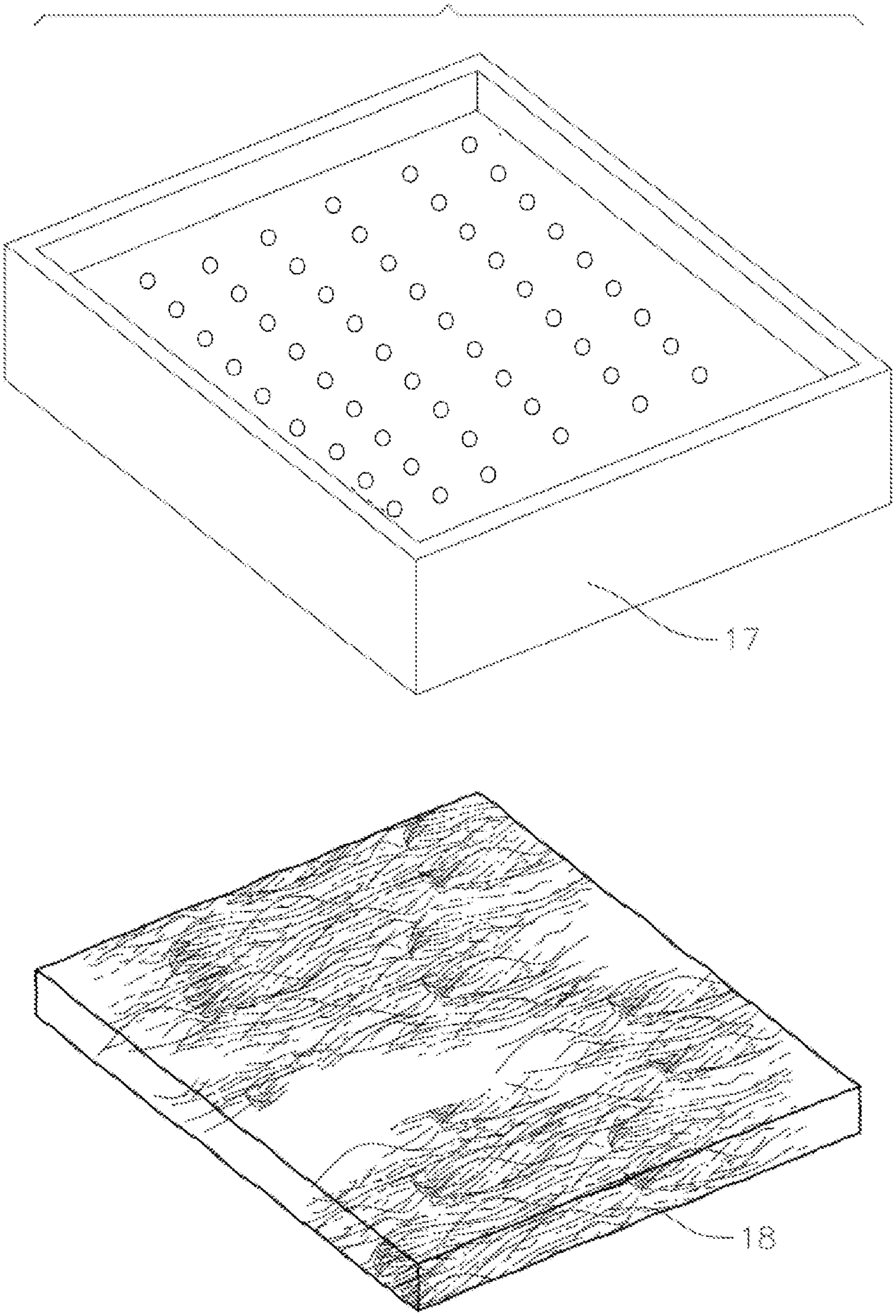
FIG. 8 shows a sheet mold (17) and sheet (18) produced from it. The thickness and density of the sheet are controlled by varying the quantity of DBF used and the spacing between the lid and the bottom of the mold, according to some embodiments of the present invention.

A simple mold of the sort shown in FIG. 8 may be used to make DBF sheets of 0.5 mm to 5 mm thick, where the mold lid may be placed on the mold (17) (the mold having holes for drainage of the liquid in the DBF slurry) where the lid is in contact with the DBF after the DBF has been wet laid and may define the degree of compression of the DBF and hence the density of the sheet.

A DBF sheet that is dried will have a low wet strength when rehydrated and improvement to the DBF sheet wet strength may be affected by placing the mold in an oven at 45-55° C. and heat treating the sheet for up to 2 hours.

In some embodiments, bone fiber pellets are formed by adding wet fibers directly into a cylindrical mold. An example of a cylindrical mold is a metal tube as is shown in FIG. 4. A bone fiber pellet shape is useful as it may be delivered to a graft site using a cannula as commonly used for minimally invasive surgery. The bone fiber pellets are capable of passing through a tube. A cylindrical mold is loaded with the fiber. A tamp is used to apply some compression to the fibers. In some embodiments, a fiber loaded cylindrical mold is dried by heat, vacuum, and/or lyophilization. After drying, the bone fiber implant becomes more cohesive and shrinks to a reduced volume. After drying, the bone fiber pellets may be easily expelled out of the mold due to the shrinkage that occurs upon drying.

While wet lay techniques may be used for the manufacture of different shapes from the bone fibers, it will be recognized that any other molding or forming technique used with textile fibers could be used. Fibers with and without excipients may be directly molded using compression into any shape. In some embodiments excipients may be selected that enhance the lubricity of the implant facilitating delivery and further reducing and friction or binding during this procedure.

Figure 7:
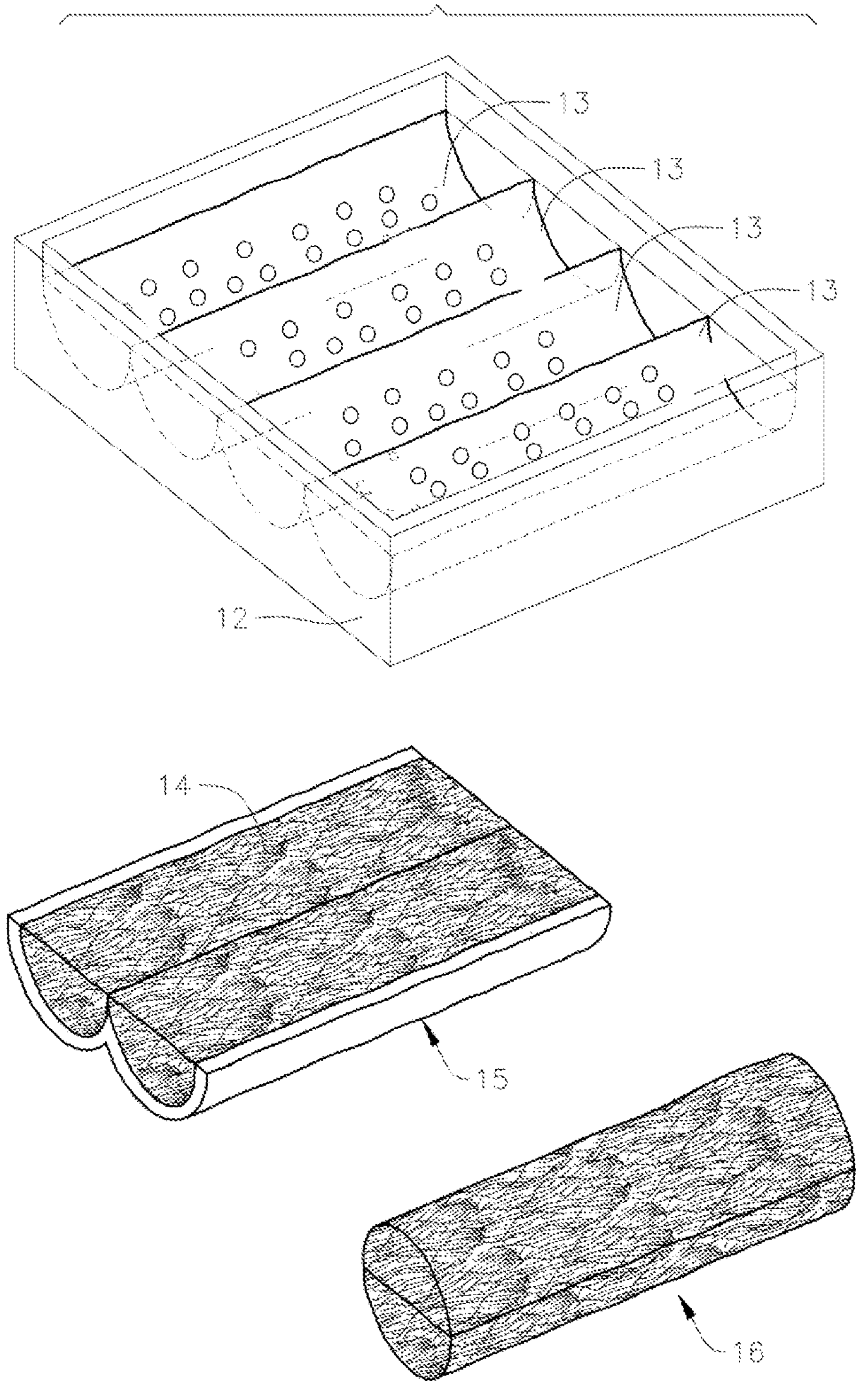
FIG. 7 shows a mold (12) with semi cylindrical depressions (13). DBF is wet laid into a mold and the implant is formed from two conjoined semi cylindrical depressions. The implants (14) may be stored in this manner in a flexible storage tray (15) and at the time of surgery may be folded together to produce a cylindrical implant (16), according to some embodiments of the present invention.

Long cylindrical implants may not be easily produced using a conventional wet lay process. As an alternative method, implants may be wet laid into a mold (12) with two conjoined semi cylindrical depressions having drainage holes throughout as shown in FIG. 7. The implants (14) may be stored in this manner in a flexible storage tray (15) and at the time of surgery may be folded together to produce a cylindrical implant (16).

Alternatively, semi cylinder implants produced in a mold such as shown in FIG. 7 may be folded together post wet lay and prior to the heat treatment step. At this time the two halves of the cylinder will become entangled and bonded to each other.

Figure 15F:
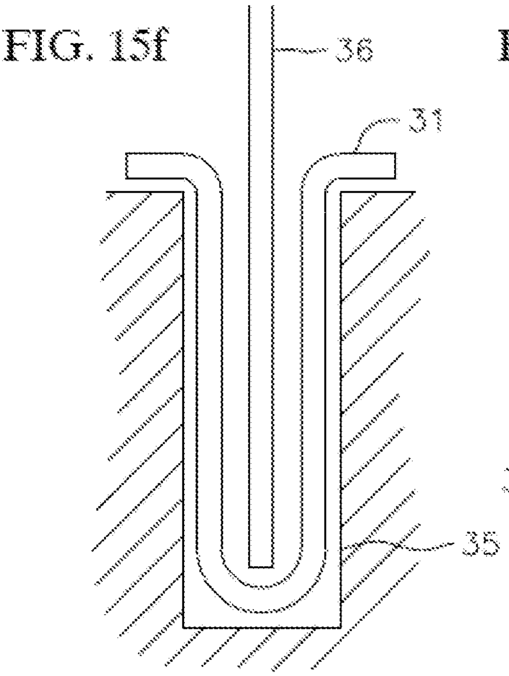
Figure 15G:
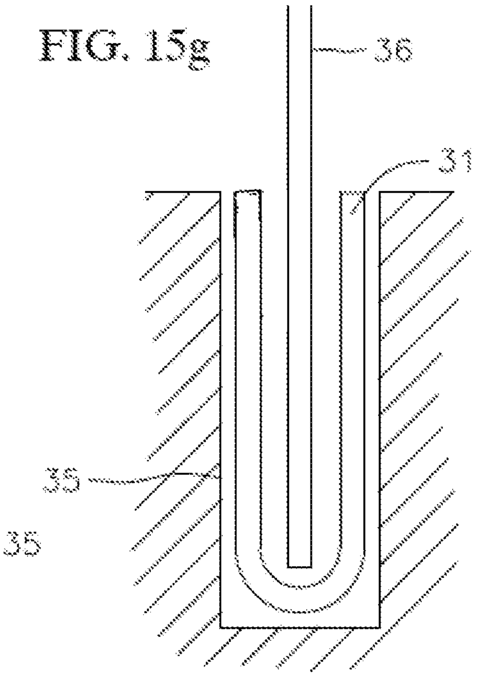
Figure 15H:
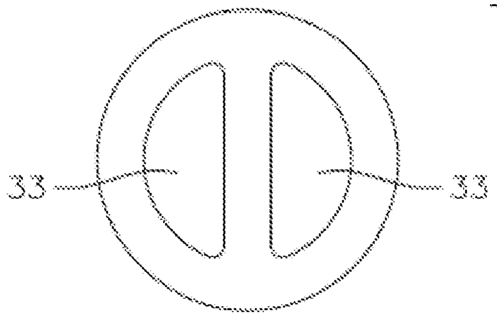
Figure 15I:
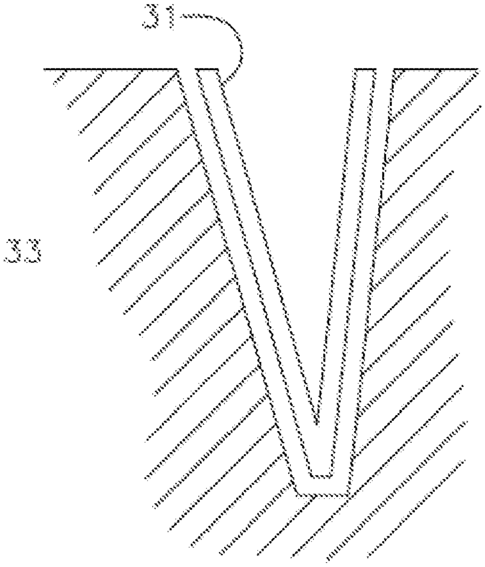

Alternatively implants for augmentation of screw fixation may be formed in two halves, such that the implant is folded about the part that becomes the implant's distal end. A selection of such designs are shown in FIGS. **15*a*-15*i*. The simplest format is a rectangular prism (31). Variants are shown as follows: in FIG. 15*b* where a central portion (32) is densified to provide it with increased strength; in FIG. 15*c* where the cross-section (33) is semi-circular; in FIG. 15*d* where the rectangular prism is narrower at the center (34); and FIG. 15*e* where the rectangular prism is both narrower at the center (34) and possesses a semi-circular cross-section (33). FIG. 15*f* shows a side view cross-section of a drill hole (35) with an implant (31) inserted, the insertion being effected by use of a pusher (36). The implant is longer than is required to fit the hole. FIG. 15*g* shows a side view cross-section of a drill hole (35) with an implant (31) inserted, the insertion being effected by use of a pusher (36) in which the implant (31) is the exact length or about the length necessary to fit in the hole without protruding out of the hole. Additionally, FIG. 15*h* is an end view looking down the hole to show that the implant shown in FIG. 15**(*c*) forms a space-filling implant when inserted into the hole. And FIG. **15*i* is a cross-sectional view of the implant of FIG. 15*e*** inserted into a tapered hole where the shape of the implant is designed to be space-filling in a tapered hole.

With continued reference to FIGS. **15*a*-15*i***, implants of these designs may be fabricated using a wet lay method with a mold that has depressions that define the required implant dimensions. The DBF is may be heated to a temperature of between 40 and 53° C. for 30 to 150 minutes to dry the implant and to improve the cohesion of the fibers. After drying the individual implants are cut out of the wet lay mold.

Using the implant designs according to embodiments of the present invention allows for facilitated insertion of the implant into holes by use of a pusher that acts upon the fold of the implant, as shown, for example in FIG. **15*b*, (32**).

There are particular difficulties that are encountered when trying to make implants of the size required to be used in augmentation of screw fixation in orthopaedic and spine surgery. The desired or required implant dimensions are approximately 2 to 7 mm diameter and 1 to 7 cm long. To enable the implant to have sufficient mechanical integrity and for the implant to be implantable, the DBF fibers must be of a sufficient size to provide a cohesive implant. The currently available DBF are approximately 4 cm long and 500 to 1000 microns wide are able to provide the mechanical integrity, however the fiber size provides a difficulty in processing the DBF into the required sizes using the heretofore-identified manufacturing methods. This problem is exacerbated when the implant is less than approximately 5 mm in diameter and is required to be longer than 1.5 cm. The fabrication of the implant of Example 1 below, while possible, was an extremely time consuming and difficult process, and is not conducive to an efficient manufacturing process. Furthermore, molding parts of the designs shown in FIGS. **15*a*-15*i*** require that the wet laid DBF is wet laid into the grooves of the mold rather than across them. If the fibers cross from one implant cavity to another then the fiber will be cut when the part is removed from the mold. If this occurs for too many fibers, then the cohesive strength of the part will be lost. For these reasons, there is a size of approximately 5 mm width, below which implants cannot be produced using this methodology.

According to embodiments of the present invention, by dispersing fibers in an excess of fluid, the fluid and fibers may be directed into molds of small diameter and long length. Implants that are 2 to 5 mm in diameter and 5 cm in length have a volume of 0.15 $cm^3$ to 0.98 $cm^3$. The required mass of DBF to fill those molds is approximately 0.15 gram to 1 gram, and may be dispersed in about 20 mls of fluid in a syringe. Any suitable fluid buffer may be used. For example, phosphate buffered saline (PBS) may be used for dispersion of the fibers as well as water or any biocompatible buffer or liquid.

FIG. 16 depicts an apparatus for water-assisted injection molding of DBF fibers. The required mass of DBF fibers (37) are loaded into a syringe (38). A suitable fluid (e.g., PBS) is then added to the syringe. The distal end of the syringe is then fitted into an adapter (39) to which is attached a detachable mold (40). The mold is the required dimensions of the implant to be made, and may be cylindrical, ribbed, or tapered. As with conventional injection molding, the cylinder will have a small taper or draft to allow removal of the molded part. The mold is tapered towards its distal end and has vents (41) along its length, and a removable vented end cap (42). The detachable mold is removed after DBF injection and placed into an oven or lyophilizer for drying. Multiple molds may be used with one adapter and syringe to allow multiple parts to be fabricated.

In some embodiments of the present invention, the ratio of fluid to DBF may be about 5 mls to 1 gram. In other embodiments, the ratio of fluid to DBF is about 10 mls to 1 gram. In still other embodiments, the ratio of fluid to DBF is greater than about 200 mls to 1 gram.

In some embodiments of the present invention, water jet assisted injection molding of DBF fibers is used. As shown in FIG. 17, the DBF fibers (37) are loaded into the hopper (43). The hopper is attached to a detachable mold (40), and the mold is tapered towards its distal end and has vents (41) along its length, and a removable vented end cap (42). A hand operated water jet (44) is activated to force the DBF from the hopper and into the mold. The detachable mold is removed after DBF injection and placed into an oven or lyophilizer for drying.

In some embodiments of the present invention, the nozzle of the water jet is about 0.1 to 1 cm in diameter, about 1 mm to 5 mm in diameter, or about 2 mm to 4 mm in diameter. The fluid flow rate may be about 1 ml/minute, 30 ml per minute, or up to about 1000 ml per minute.

The skilled person may easily envisage an apparatus with multiple funnels leading to multiple molds in a manner analogous to multi-cavity injection molds as used to fabricate injection molded polymer parts.

The implants of the present disclosure in their dry state may be inserted into a cavity, screw hold, awl hole, or drill hole. Additionally, the implants of the present disclosure may be housed in a syringe or syringe-like insertion device. With the implant in a syringe or syringe-like insertion device, the implant may have lateral stability thereby preventing or decreasing bending or buckling of the implant while it is being pushed into the surgical site (e.g., the cavity or hole).

In some embodiments of the present invention, entanglement of the DBF may be increased by stirring the fibers while in a liquid slurry. By creating a vortex, fibers are swirled and induced to become entangled. This entanglement results in non-woven 'ropes' of fibers that may be extruded and then cut to length and used as is, or further processed into pellets as described in this disclosure.

For the implants to swell post-implantation so that they are substantially space-filling, control of the processing conditions of the fibers may be controlled. For example, in some embodiments, the fibers are compressed, heated, and/or otherwise dried in order to render the fibers in a compact state such that upon wetting, the fibers are able to expand and swell.

In some embodiments of the present invention, an implant system package or implant kit includes the cylindrical molds and plunger as shown, for example, in FIG. 4.

Excipients and Additives.

Additives are contemplated to modify biological or other properties of the implant according to embodiments of the present invention. Non-limiting examples of additives include growth factors such as bone morphogenetic proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-βαs), including TGF-β-1, TGF-β-2, and TGF-β-3, and inhibitors for tumor necrosis factor (e.g., anti-TNF-α). Morphogens may also include Platelet Derived Growth Factors (PDGFs), including PDGF-A, PDGF-B, PDGF-C, PDGF-D, and GDF-5; rhGDF-5; and LIM mineralization protein, insulin-related growth factor-I (IGF-I), insulin-related growth factor-II (IGF-II), fibroblast growth factor (FGF) and beta-2-microglobulin (BDGF II), as disclosed in the U.S. Pat. No. 6,630,153, the entire contents of which is incorporated herein by reference. The polynucleotides encoding the same may also be administered as gene therapy agents. The preferred bioactive substances are the recombinant human bone morphogenetic proteins (rhBMPs) because they are available in relatively unlimited supply and do not transmit infectious diseases. In some embodiments, the bone morphogenetic protein is a rhBMP-2, rhBMP-4, rhBMP-7, or heterodimers thereof. BMPs are available from Wyeth, Madison, N.J., and may also be prepared by one skilled in the art as described in U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al., the entire contents of all of which are herein incorporated by reference.

Oxygenating additives such as perfluorocarbons may be used to further enhance the bone formation and healing of the DBF material in the implant of the present disclosure. In some embodiments, the bone repair DBF implant composition includes oxygenating materials such as a perfluorocarbon (PFC). In some embodiments, the DBF implant composition includes oxygen generating compounds such as peroxides (e.g., hydrogen peroxide, magnesium peroxide, calcium peroxide), perchlorates (e.g., sodium perchlorate, potassium perchlorate), percarbonates (e.g., sodium percarbonate), or perborates (e.g., sodium perborate).

Additionally, cancellous or cortical bone chips and/or demineralized cancellous or cortical bone chips may be added to the DBF.

Additionally, mineralized bone fibers may be added to the DBF.

Additionally, calcium phosphate, tri-calcium phosphate, hydroxyapatite, or other synthetic bone graft materials may be added to the DBF.

According to some embodiments of the present invention, introduction of an implant for screw augmentation into a patient is accomplished by placing the implant into a hole that has been drilled to receive a screw. The implant is sized to fit the hole to be repaired and to be space filling, i.e., the implant is of approximately the same length and diameter as the hole. The implant may be placed in the hole directly by hand or may be placed by use of a delivery instrument having a cylindrical element to hold the implant with a plunger to expel it.

In some embodiments of the present invention, the implant is longer than the depth of the hole to be treated and in these instances the surgeon may cut the implant to a desired length.

Forming an indentation into the end of the implant designed to receive the screw may facilitate central placement of the screw. Additionally, the implant may be tubular to further facilitate screw placement over a guide wire.

In some embodiments of the present invention, implants are formed and stored in tubes. To facilitate loading into the end of the delivery tube a recess is formed in the end of the elongated member (e.g., cannula) to hold the storage tube in correct alignment.

In some embodiments a plurality of implants are stored in a holder that is configured to attach to a delivery tube to allow easy deployment of implants.

The delivery tube may be straight or curved. In the latter instance the plunger will be flexible, being made of any suitable material, for example, nitinol wire or braided nitinol wire. The DBF implant may be shaped with a convex proximal end and concave distal end by the push rod. Alternatively implants may be introduced by separate means into the end of the delivery tube. In some instances, implants having a pellet shape may be easier to introduce into delivery tubes.

At the time of surgery, prior to implantation, a small amount of any suitable water soluble contrast agent may be injected into the implant to provide visualization during implantation. An example of a water solubler contrast agent is Iopamidol.

At the time of surgery and prior to implantation, a small amount of sterile water, phosphate buffered saline, bone marrow aspirate, and/or blood may be injected into the implant to hydrate the implant.

EXAMPLES

The following examples use cortical human bone. As discussed herein, either human or animal bone may be used as a source of cortical bone. Fibers were produced using the methodology described in U.S. Pat. Nos. 9,486,557 and 9,572,912, supra.

Example 1

1 ml disposable plastic syringes were used as a mold. The plungers were removed and 0.25 grams of DBF were introduced into the end of the syringe and the plunger used to lightly compress the fibers to a length of approximately 4 cm. The plungers were removed and the tip of the syringe cut off using a scalpel. The implants were vacuum dried overnight at 27° C. The resultant implants were approximately 4.5 mm in diameter

Example 2

Three implants from Example 1 were used to test for augmentation of screw pull out. A Sawbones 10 pores per inch foam that is frequently used to test screw pull out as a surrogate for osteopenic bone was used. Six 5 mm diameter holes were drilled in the foam block. Implants from example 1 were placed in three of the holes. 5.5 mm pedicle screws were inserted into the six holes. An MTS tensile test machine was used to record the force required to pull the screws out of the holes. The data obtained are shown in the table below.

| | Peak Force (N) | |
|---|---|---|
| | Control | Augmented |
| Test 1 | 346 | 764 |
| Test 2 | 338 | 868 |
| Test 3 | 290 | 778 |
| Average | 325 | 803 |

Example 3

15 grams of DBF fiber were wet laid in a 10 cm×11 cm flat mold to produce a sheet of DBF. The mold was heated at 55° C. for two hours to bond the fibers and dry the sheet. The sheet was approximately 1 mm thick. A portion of the sheet would be suitable for use in augmenting ACL or rotator cuff fixation.

Example 4

A portion of the sheet of Example 3 was cut to the shape of the tibial tray from a knee arthroplasty, hydrated and pressed onto the surface of the porous coated tibial tray.

Example 5

A portion of the sheet of Example 3 approximately 3 cm by 1 cm was hydrated and wrapped around the threaded portion of a 6 mm diameter pedicle screw. The DBF conformed to the surface of the screw.

Example 6

An apparatus to make implants using a water assisted injection molding (WAIM) was fabricated according to the schematic shown in FIG. 16. A 20 ml syringe with its distal end removed was placed in a 3D printed adapter. Three detachable mold sizes were used, each 5 cm long with diameters of: 3.5 mm decreasing to 3 mm; 4.5 mm decreasing to 4 mm; and 5.5 mm decreasing to 4.5 mm. DBF was placed in the 20 ml syringe and the syringe filled with PBS. The end of the syringe was placed in the adapter and the plunger pressed down to inject the DBF into the mold. DBF quantities used were 0.45 gram, 0.6 gram and 1.05 gram for the 3.5, 4.5 and 5.5 mm diameters respectively. After molding the molds were placed in a vacuum oven and dried under vacuum with a 0.5 L/min air flow overnight. After removal of the end caps the dried implants could be simply removed by pushing from the molds. The implant diameters were approximately 0.75 mm less in diameter than the mold diameter.

While the present invention has been illustrated and described with reference to certain exemplary embodiments, those of ordinary skill in the art will understand that various modifications and changes may be made to the described embodiments without departing from the spirit and scope of the present invention, as defined in the following claims.

Additionally, although relative terms such as “outer,” “inner,” “upper,” “lower,” “below,” “above,” “vertical, “horizontal” and similar terms have been used herein to describe a spatial relationship of one element to another, it is understood that these terms are intended to encompass different orientations of the various elements and components of the device in addition to the orientation depicted in the figures.

What is claimed is:

1. An implant composition, comprising:

a plurality of demineralized bone fibers (DBFs) cut from demineralized bone and molded into a shape of a tapered cylinder by water-assisted molding, wherein the implant has a distal end and a proximal end, and the distal end is narrower than the proximal end;

wherein the implant comprises a hole through its length;

wherein the implant comprises an indent at the proximal end to receive a screw; and wherein the implant in a dried state is compact and upon wetting expands and swells.

2. The implant composition of claim 1, wherein the water-assisted molding comprises 0.15 gram to 1.0 gram of DBF.

3. The implant composition of claim 1, wherein the water-assisted molding comprises a ratio of fluid to DBF in a range from about 5-200 mls fluid to about 1 gram DBF.

4. The implant composition of claim 1, wherein the implant composition has a length of from about 1 cm to about 15 cm in length.

5. The implant composition of claim 4, wherein the implant composition has a length of about 1 cm to about 7 cm.

6. The implant composition of claim 1, wherein the implant composition has a diameter of or between about 3 mm to about 15 mm.

7. The implant composition of claim 6, wherein the implant composition has a diameter of or between about 2 mm to about 7 mm.

8. The implant composition of claim 1, wherein the implant composition has a diameter of or between 2 to 5 mm and a length of or between 4 to 5 cm.

9. The implant composition of claim 1, wherein the implant composition has a volume of 0.15 $cm^3$ to 0.98 $cm^3$.

* * * * *